US00PP34158P2

(12) United States Plant Patent
Coakley

(10) Patent No.: US PP34,158 P2
(45) Date of Patent: Apr. 19, 2022

(54) ***DELPHINIUM* PLANT NAMED 'COADELPSUR'**

(50) Latin Name: *Delphinium elatum*
Varietal Denomination: COADELPSUR

(71) Applicant: Anthony Coakley, Glasgow (GB)

(72) Inventor: Anthony Coakley, Glasgow (GB)

( * ) Notice: Subject to any disclaimer, the term of this patent is extended or adjusted under 35 U.S.C. 154(b) by 0 days.

(21) Appl. No.: 17/300,869

(22) Filed: Dec. 1, 2021

(30) Foreign Application Priority Data

Dec. 2, 2020 (QZ) ..... PBR 2020/3159

(51) Int. Cl.
*A01H 5/02* (2018.01)
*A01H 6/72* (2018.01)

(52) U.S. Cl.
USPC ..... Plt./423
CPC ..... *A01H 6/72* (2018.05)

(58) Field of Classification Search
USPC ..... Plt./423
CPC ..... A01H 5/02
See application file for complete search history.

(56) References Cited

PUBLICATIONS

CPVO Citation for 'COADELPSUR' as per QZ PBR 2020/3159; Feb. 15, 2021; 3 pages.*

* cited by examiner

*Primary Examiner* — Kent L Bell
(74) *Attorney, Agent, or Firm* — Samuel R. McCoy, Jr.

(57) ABSTRACT

A new and distinct *Delphinium elatum* plant named 'COADELPSUR' which is characterized by basal foliage with compound terminal racemes held above the foliage, flowers loosely held on long pedicels, multicolored flowers with an abundance of tepaloids, and the stability and uniformity of these traits through successive cycles of asexual propagation.

3 Drawing Sheets

Latin name of the genus and species: The Latin name of the genus and species of the novel variety disclosed herein is *Delphinium elatum.*

Variety denomination: The inventive variety of *Delphinium* disclosed herein has been given the variety denomination 'COADELPSUR'.

This application claims priority to the Community Plant Variety Rights application number 2020/3159, filed on Dec. 2, 2020, which is herein incorporated by reference.

BACKGROUND OF THE INVENTION

Parentage: 'COADELPSUR' is the result of a planned breeding program carried out in Glasgow, Scotland. The claimed plant is a seedling selection resulting from the controlled pollination of a *Delphinium elatum* 'No10', the seed parent, with *Delphinium elatum* 'TC14', the pollen parent, in the summer of 2013. Both parents were developed and are owned by the inventor and were never released or patented. In the summer of 2014, one plant was observed to exhibit unique multicolored flowers with a high petaloid count and was isolated for further evaluation in order to confirm the distinctness and stability of the characteristics first observed. Upon confirmation of distinctness and stability, 'COADELPSUR' was selected for commercialization.

Asexual Reproduction: In the spring of 2015, 'COADELPSUR' was first asexually reproduced in Glasgow, Scotland by way of softwood stem cuttings. The claimed plant was found to asexually reproduce in uniform and stable manner and six successive cycles of vegetative propagation have proven to be true to type.

SUMMARY OF THE INVENTION

The following characteristics have been repeatedly observed and represent the distinguishing characteristics of the new *Delphinium* plant, 'COADELPSUR'. These traits, in combination, distinguish 'COADELPSUR' as a new and distinct cultivar.

1. 'COADELPSUR' exhibits basal foliage with a compound terminal raceme held above the foliage; and
2. 'COADELPSUR' exhibits flowers loosely held on long pedicels along the raceme; and
3. 'COADELPSUR' exhibits an abundance of tepaloids; and
4. 'COADELPSUR' exhibits flowers with multiple whorls of tightly held tepaloids at the center of the perianth, somewhat more relaxed tepaloids towards the outer whorls of the perianth, and an outer whorl of loosely held tepals; and
5. 'COADELPSUR' exhibits multicolored tepals comprised of violet-blue, blue, greyed-purple, yellow-green and green; and
6. 'COADELPSUR' exhibits light yellow-green tepaloids with a darker yellow-green central blotch near the apex; and
7. 'COADELPSUR' exhibits outermost tepaloids that are suffused with a mixture of purple-violet and violet-blue on the upper surface and colored with a mixture of violet and blue on the distal two-thirds portion of the lower surface.

BOTANICAL DESCRIPTION OF THE PLANT

Figure 1:
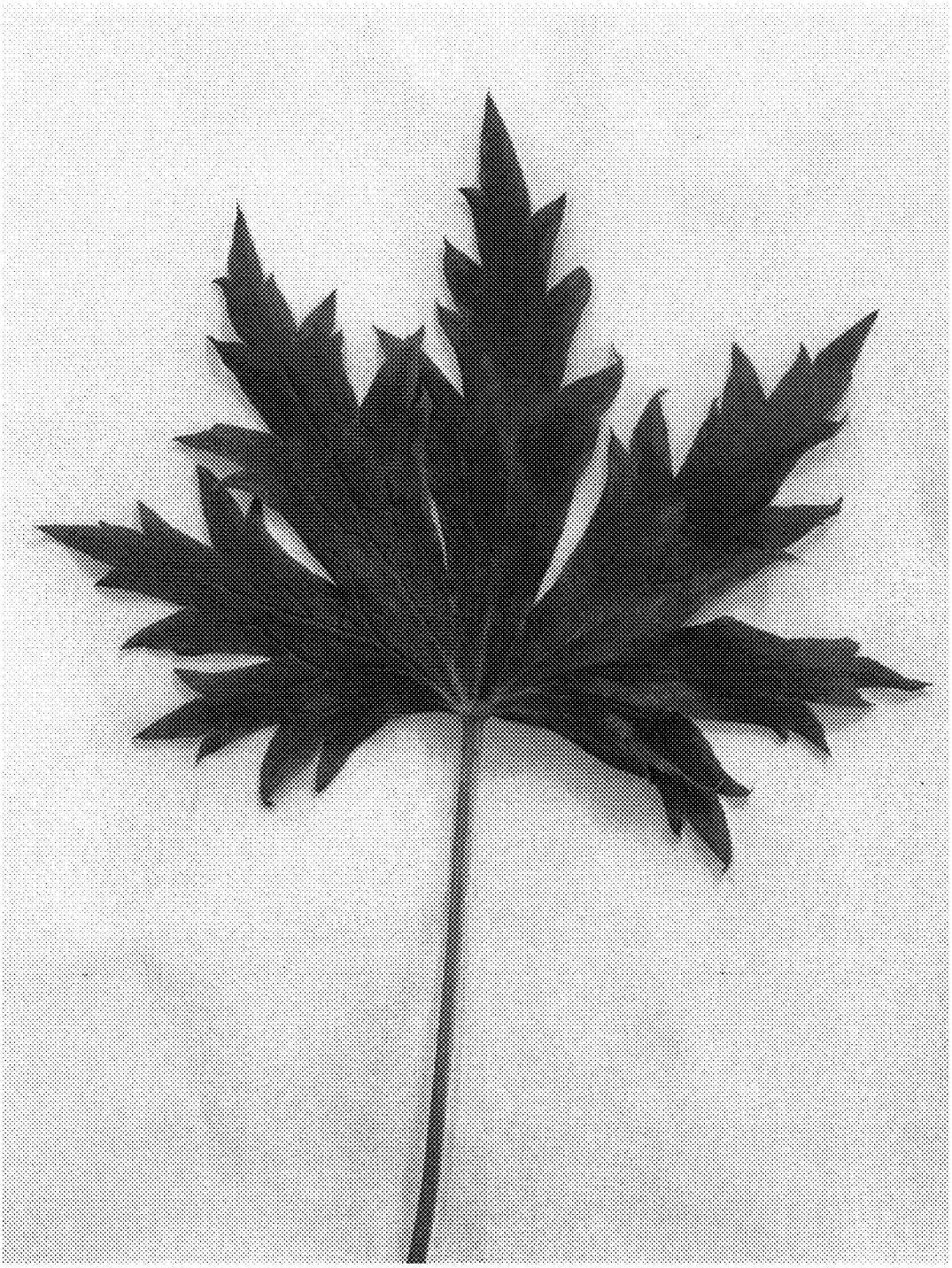
FIG. 1 illustrates, as nearly true as it is reasonably possible to make the same in color photographs of this type, the foliage of a 6-month-old 'COADELPSUR' plant.
Figure 2:
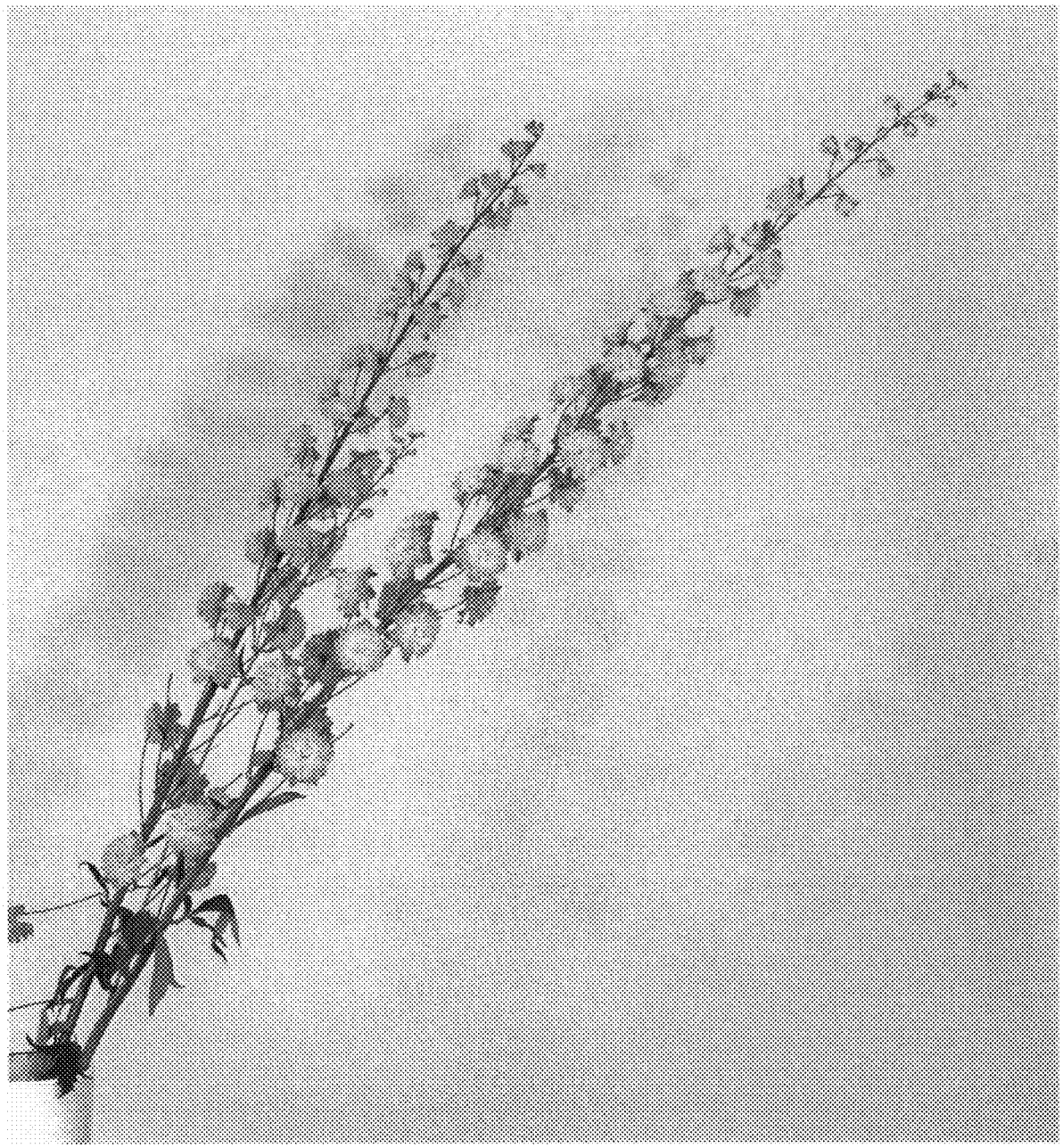
FIG. 2 illustrates, as nearly true as it is reasonably possible to make the same in color photographs of this type, the inflorescence of a 6-month-old 'COADELPSUR' plant.
Figure 3:
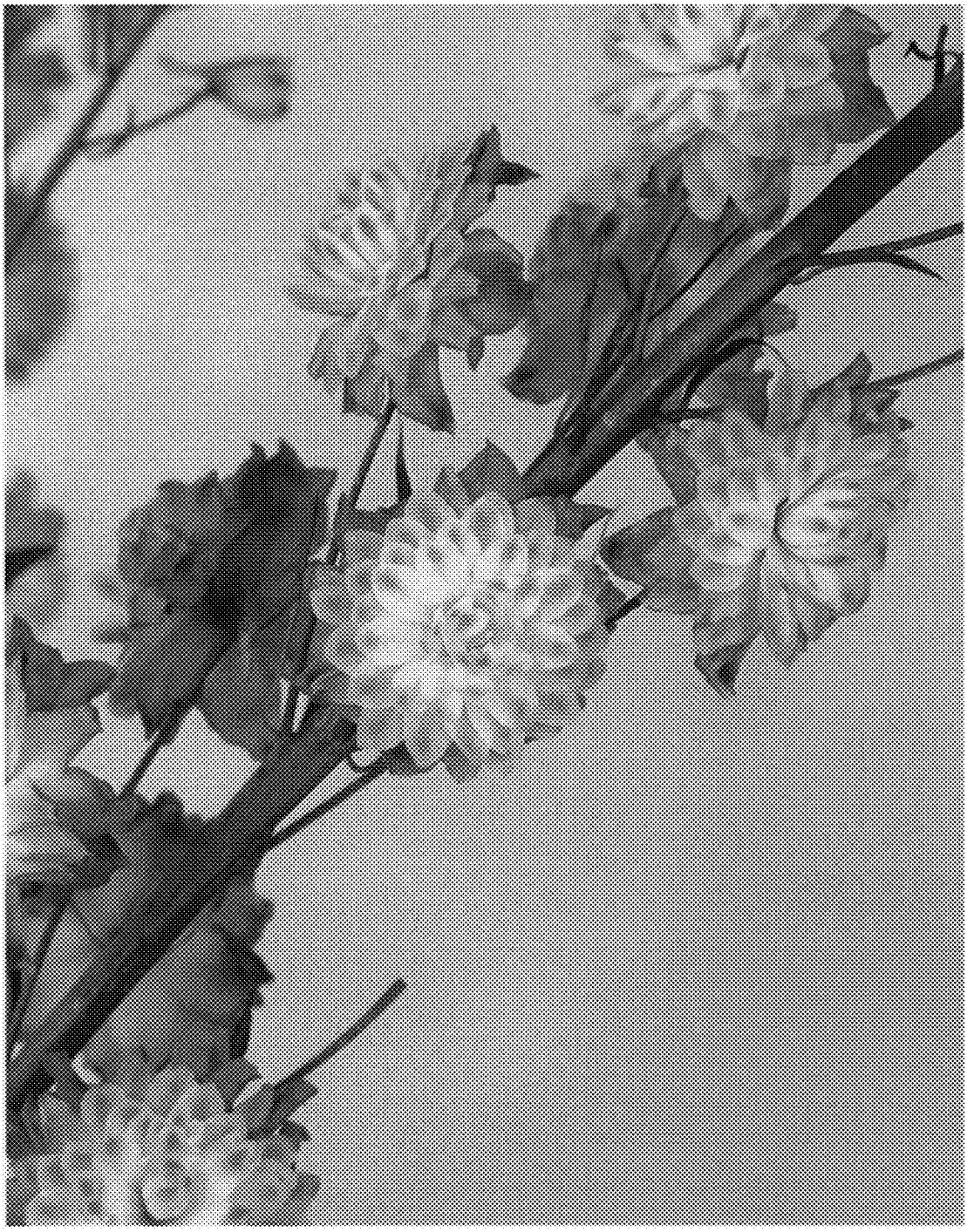
FIG. 3 illustrates, as nearly true as it is reasonably possible to make the same in color photographs of this type, the flowers of a 6-month-old 'COADELPSUR' plant.

The following is a detailed botanical description of a new and distinct *Delphinium* plant known as 'COADELPSUR'. Plant observations were made on a 6-month-old plant growing in Glasgow, Scootland. The observed plant was field-grown in full exposure to natural sunlight, maintained with organic fertilizer and overhead irrigation. Chemical control of powdery mildew was utilized in production, but no other pest or pathogen countermeasures were employed. For the purposes of these observations, the observed plant was harvested from the field and potted into a 19 cm nursery container. Observation data was recorded in July of 2021.

Those skilled in the art will appreciate that certain characteristics will vary with older or, conversely, younger plants. 'COADELPSUR' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, Sixth Edition except where common terms of color are used.

A botanical description of 'COADELPSUR' and comparisons with the parents and most similar commercial cultivar are provided below.

General plant description:

*Plant habit*.—Perennial plant with basal foliage and branched flowering stems, bearing flowers arranged on terminal racemes held above the foliage.

*Plant profile*.—Narrow ovate to ovate.

*Height*.—48.1 cm to the top of the foliar plane; 132.2 cm to the top of the floral plane.

*Plant vigor*.—Moderately vigorous.

*Growth rate*.—Fast growing.

*Propagation*.—Method — Softwood stem cuttings. Time to initiate rooting — 6 weeks at an average ambient temperature of 15 degrees Celsius. Time to produce flowering plant from rooted cutting — Approximately 6 months in an 11 cm container.

*Pest resistance and susceptibility*.—Not any more or less susceptible to pests or diseases known to effect *Delphinium* sp.

*Environmental tolerances*.—Adapt to, at least, USDA Zones 5 to 9 and temperatures ranging from minus 23 degrees Celsius to 35 degrees Celsius; moderate tolerance to rain; low tolerance to wind.

Root system:

*Description*.—A moderately dense network of relatively shallow thin, fibrous feeder roots and deeper thick anchor roots.

Stems:

*Branching habit*.—No vegetative branches are present, however branched flowering stems are present.

*Flowering stem*.—Attitude — Erect; near vertical. Aspect — Generally rounded; very slightly angular. Strength — Strong. Length — 38.8 cm. Diameter — 1.0 cm. Internode length — 4.6 cm. Texture — Glabrous. Luster — Matte, due to the presence of epicuticular wax. Color, developing stems — Yellow-green, nearest to RHS 144A. Color, mature stems — Yellow-green, nearest to RHS 146A, and covered with an epicuticular wax which is colored greyed-green, nearest to RHS 191A. Color at the internodes — Yellow-green, nearest to RHS 146A, and covered with an epicuticular wax which is colored greyed-green, nearest to RHS 191A.

Foliage:

*Arrangement*.—Alternate.

*Attachment*.—Petiolate.

*Division*.—Simple.

*Quantity*.—14 stem leaves.

*Shape*.—Palmate with a reniform outline; deeply lobed to near cleft.

*Lobes*.—Depth of sinuses — Deep. Sinus orientation — Divergent.

*Aspect*.—Flat.

*Attitude*.—Outward.

*Length*.—14.5 cm.

*Width*.—17.7 cm.

*Apex*.—Narrowly acute.

*Base*.—Broadly hastate; lobes free.

*Margins*.—Coarsely serrate; sparsely to moderately pubescent.

*Texture and pubescence, adaxial surface*.—Smooth and glabrous.

*Texture and pubescence, abaxial surface*.—Smooth and glabrous with the exception of the veins which are sparsely to moderately covered with short, soft hairs. Hairs have an average length of 0.75 mm and are colored white, nearest to RHS NN155D.

*Luster, adaxial surface*.—Slightly glossy.

*Luster, abaxial surface*.—Slightly glossy.

*Color*.—Juvenile foliage color, adaxial surface — Green, nearest to a mixture of RHS 138A and 143A. Juvenile foliage color, abaxial surface — Yellow-green, nearest to RHS 146A. Mature leaf color, adaxial surface — Green, nearest to RHS NN137A. Mature leaf color, abaxial surface — Yellow-green, nearest to RHS 147B.

*Venation*.—Type — Laciniate. Vein color, adaxial surface — Yellow-green, nearest to RHS 144A. Vein color, abaxial surface — Yellow-green, nearest to a mixture of RHS 146A and 146B.

*Petiole*.—Length — 13.3 cm. Diameter — Petioles are flattened; 0.3 cm tall and 0.25 cm wide. Strength — Very strong. Texture, adaxial and abaxial surfaces — Smooth and sparsely covered with very short, soft hairs at both the distal and proximal ends. Hairs exhibit an average length of 1.5 mm. Luster, adaxial and abaxial surfaces — Moderately glossy. Color, adaxial surface — Yellow-green, nearest to RHS 146A, and suffused with a darker shade of yellow-green towards the proximal end, nearest to RHA 152A. Color, abaxial surface — Yellow-green, nearest to RHS 144A.

*Stipules*.—None.

Inflorescence:

*Inflorescence type*.—Compound terminal raceme with a central, main raceme and lateral racemes.

*Natural flowering season*.—Late summer in Glasgow, Scotland.

*Time to flower or response time*.—Approximately 9 months.

*Height*.—The entire compound raceme is 99.4 cm high, from the lowest branching of the peduncle to the apex of the inflorescence. The main, central raceme is 91.9 cm tall.

*Diameter*.—The entire compound raceme is 22.6 cm in diameter; the main, central raceme is 12.2 cm in diameter.

*Quantity of flowers per inflorescence*.—52 on the main raceme; 21 on the lateral raceme.

*Peduncle*.—Length — Approximately 98.2 cm. Diameter — Approximately 0.6 cm. Attitude — Erect, in an average angle of 0 degrees to the main stem. Strength — Strong. Texture — Smooth, glabrous, and glaucous. Luster — Matte. Color — Yellow-green, nearest to RHS 144A; epicuticular wax is green, nearest to RHS 138A.

*Bracts*.—Quantity — Two bracts are present at the base of each individual flower. Arrangement — Opposite. Shape — Linear. Length — 1.8 cm, on average. Width — 0.1 cm, on average. Apex — Narrowly acute. Base — Cuneate. Margin — Entire. Texture — Smooth and glabrous. Color, adaxial and abaxial surfaces — Yellow-green, nearest to 144A.

Flower bud:

*Shape*.—Broad obovate, excluding the floral spur.

*Length*.—Average of 1.4 cm, excluding the spur; 2.3 cm, including the spur.

*Diameter*.—1.0 cm.

*Texture*.—Smooth and glabrous.

*Luster*.—Very slightly glossy.

*Color, upper surface*.—Yellow-green, nearest to RHS 145C, and darker at the apex, nearest to RHS 144A; suffused with greyed-green, nearest to RHS 194B.

*Color, lower surface*.—Yellow-green, nearest to RHS 145C, and darker at the apex, nearest to RHS 144A.

*Color, spur*.—Greyed-green, nearest to RHS 194B.

Flower:

*Type and form*.—Rotate; double.

*Aspect*.—Outwardly to slightly upright.

*Flowering habit*.—Freely flowering.

*Flower longevity on plant*.—Approximately 10 days.

*Longevity of cut flowers*.—Approximately 10 days.

*Persistent or self-cleaning*.—Self-cleaning

*Fragrance*.—Non-fragrant.

*Height*.—Average of 5.6 cm.

*Width*.—Average of 4.9 cm.

*Depth*.—Average of 4.1 cm.

*Perianth*.—No distinct petals and sepals, only tepals and tepaloids are present. Tepals — Quantity — 5 unfused tepals; one dorsal, two lateral, and two lower tepals. Arrangement — Rotate; single whorl. Attitude — Relaxed. Aspect — Moderately concave. Length — Dorsal tepal — 2.7 cm. Lateral tepals — 2.7 cm. Lower tepals — 2.8 cm. Width — Dorsal tepal — 1.6 cm. Lateral tepals — 1.7 cm. Lower tepals — 1.5 cm. Shape — Dorsal tepal is elliptic; lateral tepals are obovate; lower tepals are narrowly obovate to elliptic. Apex — Doral tepal is acute; lateral and lower tepals are broadly acute to acute. Base — All tepals are broad cuneate. Margin — All tepals are entire and slightly undulated. Texture, luster and pubescence of the upper surface — All tepals are glabrous, moderately velvety, and matte. Texture, luster and pubescence of the lower surface — All tepals are glabrous, slightly velvety, and matte. Color when opening, upper surface — Dorsal tepal — Violet-blue, nearest to RHS 98B; suffused with yellow-green in the central zone of the tepal, nearest to RHS 147C; proximal one-half portion of the tepal is a translucent yellow-green, nearest to RHS 147D. Lateral tepals — Yellow-green, nearest to RHS 145C, and fading to a slightly lighter shade of yellow-green towards the margins, nearest to RHS 145D; becoming darker at the base, nearest to RHS 144A; apex is blue, nearest to a mixture of RHS 100A and 100B. Lower tepals — Yellow-green, nearest to RHS 145C, and fading to a slightly lighter shade of yellow-green towards the margins, nearest to RHS 145D; becoming darker at the base, nearest to RHS 144A; apex is blue, nearest to a mixture of RHS 100A and 100B. Color when opening, lower surface — Dorsal tepal — The distal one-half portion of the tepal is green, nearest to RHS 143B; the proximal half of the tepal is a translucent greyed-green, nearest to RHS 195C, and fades to yellow-green at the base, nearest to RHS 144B; margined blue, nearest to RHS 102D. Lateral tepals — Yellow-green, nearest to RHS 144A, and fading to a slightly lighter shade of yellow-green towards the base, nearest to a mixture of RHS 145A and 145B, before again darkening slightly at the base, nearest to RHS 144A; margins are yellow-green, RHS 145D, and transition to blue along the distal portion of the margins and apex, nearest to RHS 100B. Lower tepals — Yellow-green, nearest to RHS 144A, and fading to a slightly lighter shade of yellow-green towards the base, nearest to a mixture of RHS 145A and 145B, before again darkening slightly at the base, nearest to RHS 144A; margins are yellow-green, RHS 145D, and transition to blue along the distal portion of the margins and apex, nearest to RHS 100B. Color when fully opened, upper surface — Dorsal tepal — Violet-blue, nearest to RHS 98B; suffused with yellow-green in the central zone of the tepal, nearest to RHS 144A; apex is greyed-green, nearest to RHS 197A; proximal one-half portion of the tepal is a translucent green-white, nearest to RHS 157C; base is yellow-green, nearest to RHS 144B. Tepals do not fade with age. Lateral tepals — The distal one-half portion of the tepal is blue, nearest to RHS 100B, and suffused with green towards the central zone, nearest to a mixture of RHS 133B and 133C; tepal color transitions to a mixture of violet-blue and greyed-purple towards the base, nearest to RHS 91D and N187D; base is colored yellow-green, nearest to RHS 146D. Tepals do not fade with age. Lower tepals — The distal one-half portion of the tepal is blue, nearest to RHS 100B, and suffused with green towards the central zone, nearest to a mixture of RHS 133B and 133C; tepal color transitions to a mixture of violet-blue and greyed- purple towards the base, nearest to RHS 91D and N187D; base is colored yellow-green, nearest to RHS 146D. Tepals do not fade with age. Color when fully opened, lower surface — Dorsal tepal — Violet-blue, nearest to RHS 94C; fading to green towards both the base and apex, nearest to RHS 143C; apex is grey-brown, nearest to RHS 199B. Tepals do not fade with age. Lateral tepals —

Violet-blue, nearest to RHS 91D, and fading to yellow-green towards the central zone of the tepal, nearest to a mixture of RHS 144A, 144B and 144C; base is yellow- green, nearest to RHS 146C; margins are blue, nearest to RHS 100B. Tepals do not fade with age. Lower tepals — Violet-blue, nearest to RHS 91D, and fading to yellow-green towards the central zone of the tepal, nearest to a mixture of RHS 144A, 144B and 144C; base is yellow-green, nearest to RHS 146C; margins are blue, nearest to RHS 100B. Tepals do not fade with age. Tepal venation color — Fully opened, upper surface — Yellow-green, nearest to RHS 146C. Fully opened, lower surface — Yellow-green, nearest to RHS 146C. Tepaloids — Arrangement — Rotate; the unfused tepaloids are relatively tightly-held in 10 whorls. Attitude — Inner tepaloids are erect; outer tepaloids are somewhat relaxed. Aspect — Inner tepaloids are strongly concave; outer tepaloids are reflexed. Quantity — 90. Length — 2.0 cm. Width — 0.9 cm. Shape — Obovate to narrowly obovate. Apex — Acute. Base — Cuneate. Margin — Entire; slight, coarse undulation. Texture, luster and pubescence of the inner surface — Moderately velvety, glabrous and matte. Texture, luster and pubescence of the outer surface — Slightly velvety, glabrous and very slightly glossy. Color when opening, upper surface — Yellow-green, nearest to RHS 144A, and fade to a lighter shade of yellow-green towards the margins, nearest to a mixture of RHS 145C and 145D. Outer tepaloids are suffused with blue-green, nearest to a mixture of RHS 116B and 116C. Color when opening, lower surface — Yellow-green, nearest to RHS 144A, and fading to a lighter shade of yellow-green towards the margins, nearest to a mixture of RHS 145C and 145D. Apex of outer tepaloids are green, nearest to RHS 143A. Color when fully opened, upper surface — Yellow-green, nearest to a mixture of RHS 145A and 145D, with a darker yellow-green central blotch near the apex, nearest to RHS 144A. Outer tepaloids are heavily suffused with a mixture of purple-violet and violet-blue, nearest to a mixture of RHS N82B, 94A and 96D. Tepaloids do not fade with age. Color when fully opened, lower surface — Yellow-green, nearest to a mixture of RHS 145C and 145D, with a darker yellow-green central blotch near the apex, nearest to RHS 144A. The distal two-thirds portion of the outer tepaloids are colored with a mixture of violet and blue, nearest to RHS N87C, 100A and 100B. Tepaloids do not fade with age. Tepaloid venation color when fully opened, inner surface — Yellow-green, nearest to RHS 145A. Tepaloid venation color when fully opened, outer surface — Yellow-green, nearest to RHS 145A. Pedicels — Length — 8.5 cm. Diameter — 0.175 cm. Angle — Average angle to peduncle axis is approximately 40 degrees. Strength — Moderately strong to strong. Texture — Smooth and glabrous. Luster — Glossy. Color — Green, nearest RHS 143A. Spurs — Quantity — One dorsal tepal spur present. Length — 1.9 cm. Diameter — 0.3 cm. Shape — Narrowly oblanceolate. Apex — Obtuse. Base — Broad cuneate. Texture — Moderately rugose and glabrous. Luster — Moderately glossy. Color — Greyed-green, nearest to RHS 195B; slightly suffused with greyed-purple, nearest to RHS N187D.

Reproductive organs: All reproductive organs reduced to tepaloids. An undeveloped ovary is present; colored green, nearest to RHS 143A.

Fruit and seed: No fruiting has been observed.

COMPARISON WITH THE PARENT PLANT

Plants of the new cultivar 'COADELPSUR' differ from the seed parent, *Delphinium elatum* 'No10' (not patented), by the characteristics described in Table 1.

TABLE 1

| Characteristic | 'COADELPSUR' | 'No10' |
|---|---|---|
| Quantity of tepaloids. | More than 'No10'. | Fewer than 'COADELPSUR'. |

Plants of the new cultivar 'COADELPSUR' differ from the pollen parent, *Delphinium elatum* 'TC14' (not patented), by the characteristics described in Table 2.

TABLE 2

| Characteristic | 'COADELPSUR' | 'TC14' |
|---|---|---|
| Quantity of tepaloids. | More than 'TC14'. | Fewer than 'COADELPSUR'. |

COMPARISON WITH THE MOST SIMILAR *DELPHINIUM* CULTIVAR KNOWN TO THE INVENTOR

Plants of the new cultivar 'COADELPSUR' are most similar to the commercial cultivar, *Delphinium elatum* 'Dolce Vita' (U.S. Plant Pat. No. 13,010). A comparison of 'COADELPSUR' with *Delphinium* 'Dolce Vita' is described in Table 3.

TABLE 3

| Characteristic | 'COADELPSUR' | 'Dolce Vita' |
|---|---|---|
| Plant size. | Taller than 'Dolce Vita'. | Shorter than 'COADELPSUR'. |
| Foliage size. | Smaller than 'Dolce Vita'. | Larger than 'COADELPSUR'. |
| Inflorescence size. | Longer than 'Dolce Vita'. | Shorter than 'COADELPSUR'. |
| Arrangement of flowers. | Loosely held along the peduncle, on pedicels that are longer than those of 'Dolce Vita'. | Tightly arranged on shorter pedicels, along the length of the peduncle. |
| Presence of reproductive organs. | None present; All reproductive organs reduced to tepaloids. | Present. |
| Quantity of tepaloids. | 90. | 17. |
| General coloration of the tepals when fully opened; upper surface. | Inner tepaloids are generally pale yellow-green; outer tepaloids are pale yellow-green and heavily suffused with a mixture of purple-violet and violet-blue. | Light purple and lightly suffused with white; margined blue. |

That which is claimed is:

1. A new and distinct variety of *Delphinium elatum* plant named 'COADELPSUR', substantially as described and illustrated herein.

* * * * *